Figure 6:
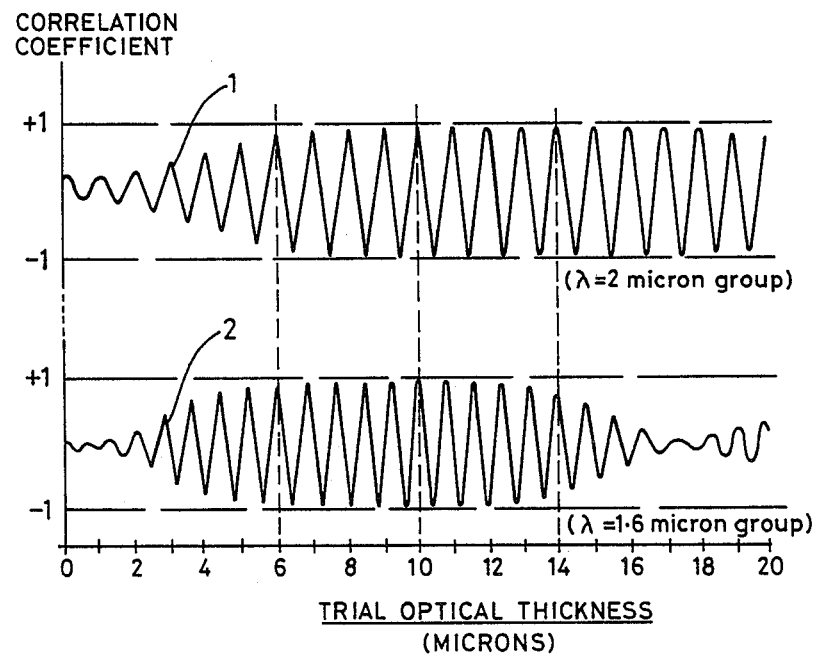

United States Patent [19]

Edgar et al.

[11] Patent Number: 4,885,709

[45] Date of Patent: Dec. 5, 1989

[54] METHOD AND APPARATUS FOR SENSING OR DETERMINING ONE OR MORE PROPERTIES OR THE IDENTITY OF A SAMPLE

[75] Inventors: Roger F. Edgar, Maldon; Peter H. Hindle, Hatfield Peverel, both of England

[73] Assignee: Infrared Engineering Limited, Maldon, England

[21] Appl. No.: 4,347

[22] Filed: Jan. 16, 1987

[30] Foreign Application Priority Data

Jan. 17, 1986 [GB] United Kingdom ............... 8601176

[51] Int. Cl.$^4$ .................... G01N 23/16; G01B 15/02
[52] U.S. Cl. .................... 364/563; 356/432; 356/382; 364/524; 250/358.1
[58] Field of Search ........... 364/524, 526, 563; 356/382, 432; 358/75, 80, 93; 250/225, 560

[56] References Cited

U.S. PATENT DOCUMENTS

| | | | |
|---|---|---|---|
| 3,955,086 | 5/1976 | Tsujii et al. | 364/563 X |
| 4,017,192 | 4/1977 | Rosenthal | 356/432 |
| 4,194,217 | 3/1980 | van den Bosch | 358/93 |
| 4,355,903 | 10/1982 | Sandercock | 356/382 |
| 4,414,635 | 11/1983 | Gast | 364/526 |
| 4,510,577 | 4/1985 | Tsujii et al. | 364/563 |
| 4,513,384 | 4/1985 | Rosencwaig | 364/563 |
| 4,555,767 | 11/1985 | Case et al. | 364/563 |
| 4,574,387 | 3/1986 | Gignoux et al. | 364/563 X |
| 4,672,196 | 6/1987 | Canino | 250/225 |
| 4,676,647 | 6/1987 | Kikkawa et al. | 356/382 |
| 4,687,333 | 8/1987 | Odasima et al. | 356/382 |
| 4,717,954 | 1/1988 | Fujita et al. | 358/80 |

FOREIGN PATENT DOCUMENTS 0114515 8/1984 European Pat. Off. .
1420298 1/1976 United Kingdom .

OTHER PUBLICATIONS

"A New Method for Obtaining Individual Component Spectra from those of Complex Mixtures", D. E. Honigs, G. M. Hieftje and T. Hirschfeld, pp. 317–322, 1369 Spectroscopy 38 (1984) May/Jun., No. 3, Baltimore, Md., U.S.A.

"Transparent Film Thickness Measurement", W. R. Case and W. E. Johnson, vol. 24, No. 1A, Jun., 1981, IBM Technical Disclosure Bulletin.

Hewig et al: In-Situ, Real Time Thin Film Refractive Index and Thickness Monitor, IBM Technical Disclosure Bulletin, vol. 25. No. 1, Jun., 1982, pp. 436–438.

*Primary Examiner*—Felix D. Gruber
*Attorney, Agent, or Firm*—Leydig, Voit & Mayer

[57] ABSTRACT

In the method and apparatus, optimum correlation between measured and known values of transmittance or reflectance determines the property or identity of a sample. Three or more discrete radiation components can be selected which are transmitted or reflected by relatively different amounts due to interference, absorption or scatter, thereby enabling fewer radiation components to be used to provide an accurate result. The known values can be derived by analogue or digital techniques, the digital technique employing a model or models taking account of absorption, interference and/or scatter. Techniques are disclosed for reducing computing time by range ajustment, identification of a zero correlation value in a differential function of the model or models and computation of correlation coefficients for two or more groups of radiation components.

35 Claims, 3 Drawing Sheets

OPTICAL TRANSMISSION
GAUGING APPARATUS

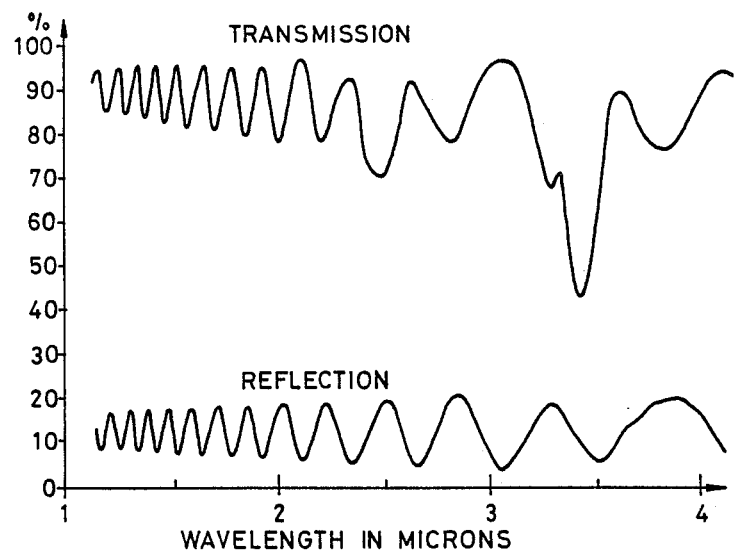
Fig. 1  REFLECTION AND TRANSMISSION SPECTRA OF A THIN ORGANIC FILM.
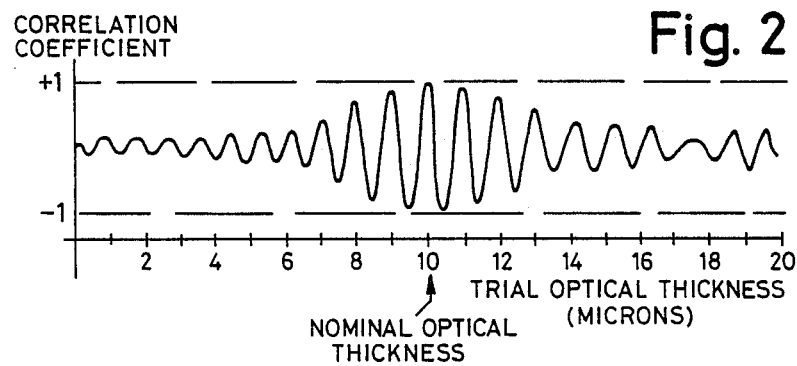
Fig. 2
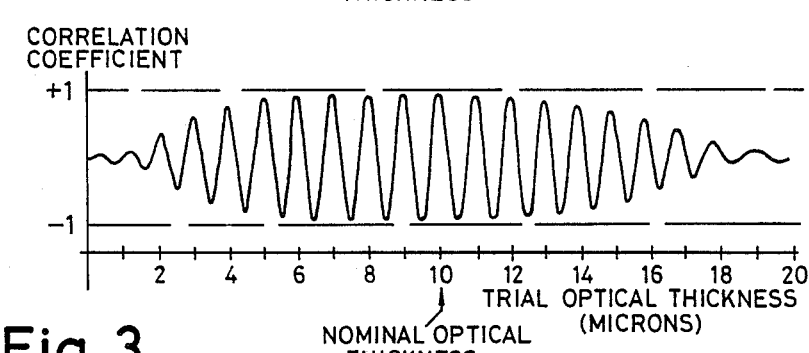
Fig. 3

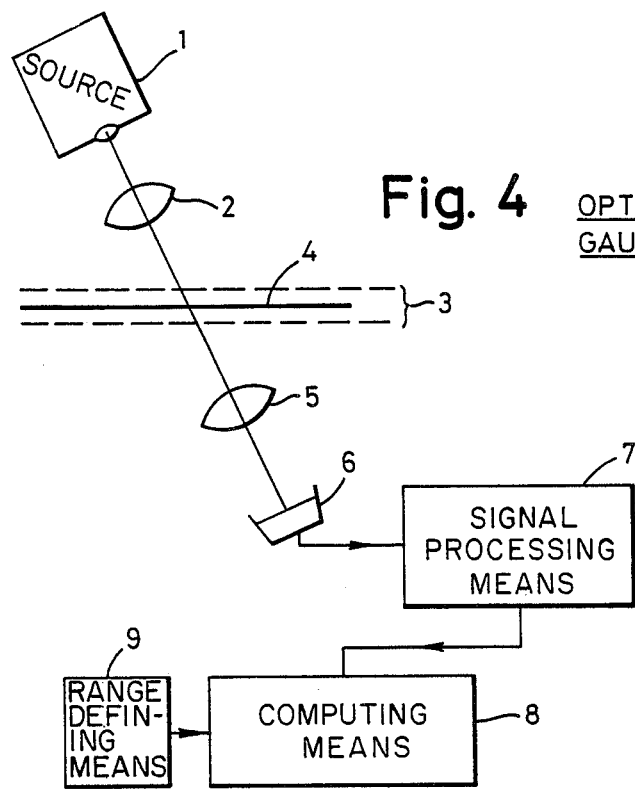
Fig. 4  OPTICAL TRANSMISSION GAUGING APPARATUS
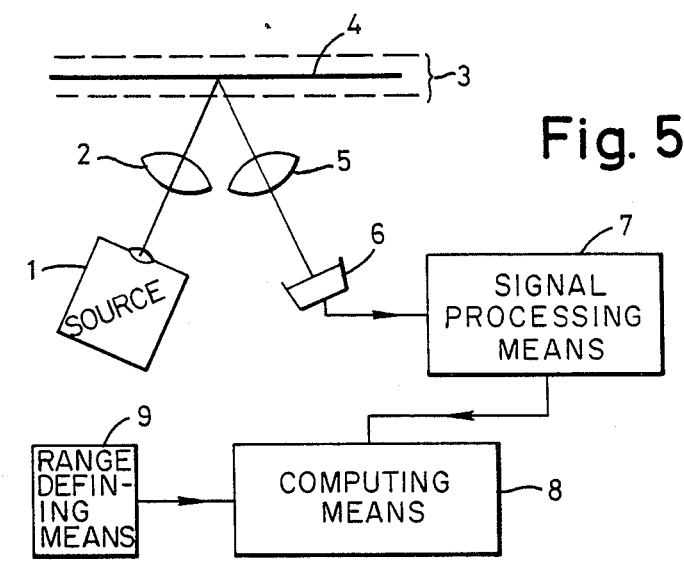
Fig. 5
OPTICAL REFLECTION GAUGING APPARATUS

METHOD AND APPARATUS FOR SENSING OR DETERMINING ONE OR MORE PROPERTIES OR THE IDENTITY OF A SAMPLE

This invention relates to a method and apparatus for sensing or determining one or more properties, or the identity of a sample in which electromagnetic radiation is subject to optical interference, absorption or scatter. The sample may be in a solid, liquid, or gaseous phase or it may contain materials in different phases. The invention is particularly, but not exclusively useful in determining the properties or constituents of a film, coating, layer, laminate or a constituent layer of a laminate. For example, the invention may be applied to determine the thickness of a plastics film produced by a continuous process, or to sense a change in optical anisotropy in a film of plastics which is stretched during manufacture, the stretching being controlled with regard to sensed value. The invention can also be applied, inter-alia, to determine the composition or structure of a sample, to measure the quantity of material sorbed onto the surface of granular material, to measure the depth of coating on fibres, such as textiles, threads and yarns, to identify material of a sample and to measure or detect other physical parameters which vary and thereby give rise to changes in the optical properties of a sample. The invention may be used to improve accuracy of techniques which depend on either optical interference, absorption or scatter in order to derive a measured or sensed value. However, the invention can provide a particular advantage with absorption techniques, since it substantially eliminates errors due to optical interference effects.

For interference measurement to be possible, the optical thickness of the sample must be substantially less than the coherence length of the radiation used and the sample surfaces, over the area to be measured, must be flat and parallel within a range of values significantly less than about 1/6th of the shortest wavelength of radiation used in the measurement. Hence, optical interference techniques are not always practical.

Optical interference techniques need not be used to measure properties such as film thickness. For example, optical absorption techniques are commonly carried out in the infrared region of the spectrum, particularly to take measurements of organic materials which exhibit absorption characteristics in this spectral region. Optical absorption gauges are known in the art to determine the thickness or composition of films, coatings, laminates and components of laminates. With such gauges, two or more beams of radiation, each having a narrow bandwidth centered on relatively different wavelengths, are passed through a sample of material and the respective transmittance of each beam is sensed by means of a photoelectric detector. With two beams, for example, the wavelengths are selected so that one beam is weakly absorbed, whilst the other is strongly absorbed. A ratio of the respective detector signals can then be computed to provide a measure of, e.g. the thickness or moisture content of a sample (such techniques are well known and hence no detailed description is required).

Whilst optical absorption techniques are advantageous in simplifying the equipment required to make accurate measurements, problems occur under certain circumstances leading to measurement inaccuracies. For example, when the optical thickness of the sample is less than, or comparable with the coherence length of the respective wavebands of the radiation used, and when the surfaces of the sample are flat and parallel to within a range of values less than about 1/6th of the centre wavelength of any of the wavebands, then errors will occur in measured transmittance due to optical interference effects. These effects cause changes in the transmitted intensities of the beams and such changes are not directly related to, e.g. a variation in the thickness to be measured. Moreover, these interference effects are likely to cause greater measurement errors when trying to measure the thickness of very thin films, because strong interference effects then occur over a range of thickness values tending to obscure the measurement of true thickness. Although interference effects may be countered by broadening the spectral bandwidths of the beams of radiation, the degree of broadening necessary to reduce optical interference errors to acceptably low levels has the secondary effect of reducing differential changes in the transmitted intensities of the beams to a level at which photometric errors will degrade the precision of measurement. Therefore, spectral bandwidth broadening does not solve the problem of optical interference when using absorption techniques.

The requirements for making accurate measurements with optical absorption techniques are substantially opposite to those with optical interference techniques. Whilst absorption techniques are generally preferred with industrial processes, the different requirements for absorption and interference techniques still gives rise to certain problems. For example, many products which are manufactured are made of material which is either too thin and insufficiently variable to suppress optical interference effects and to permit absorption measurement, and yet that material is too thick and too variable to permit satisfactory measurement by interference techniques. One of the aims of a preferred embodiment of the invention is to provide a method and apparatus which work in the latter-mentioned region of intermediate quality and thickness in which a sample is too thick for interference effects to be used accurately and too thin for absorption effects to be used accurately.

A more general aim of the invention is to improve measurement accuracy, particularly with absorption techniques where interference errors are likely to obscure the sensing or determination of a particular property, or identity of a sample. In achieving this aim, the invention enables the use of absorption techniques in situations where interference techniques were previously thought to be necessary for greater accuracy. Hence the invention enables the more complex optical interference equipment to be replaced by the less complex optical absorption equipment thereby reducing expense and maintenance.

US-A-4555767 discloses a method and apparatus for measuring the thickness of an epitaxial layer by infrared reflectance. A Fourier transform infrared spectrometer is used to provide measured values of spectral reflectance and these measured values are correlated with a series of theoretical reflectance values which have been determined for different thicknesses in a range including a nominal thickness. The actual thickness of the epitaxial layer is determined from the correlation analysis. A problem associated with the system disclosed by this reference is that a relatively long computing time is necessary to obtain an accurate result. This is due to the use of a large number of regularly spaced wavelengths. For example, the reference teaches that a typical system employs 125 wavelengths equally spaced across the IR spectrum of 2.5 to 50 microns. A long computing time is undesirable particularly where accurate results are rapidly required as in the case of continuous industrial processes. For example, in continuous film manufacture the thickness of a rapidly moving film needs to be determined quickly to provide adequate control of the process. Besides this problem, the Fourier IR spectrometer is more suitable for taking measurements in the laboratory than in most industrial processes and its cost, complexity and the need for a large number of wavelengths mean that it is unsuitable for most industrial environments. There is therefore a need for a less complicated, cheaper and more robust instrument which is still capable of giving accurate results. The invention also seeks to solve these problems.

According to one aspect of the present invention, a method of sensing or determining one or more properties or the identity of a sample in which electromagnetic radiation is subject to optical interference, absorption or scatter, comprises the steps of:

(a) causing electromagnetic radiation to be transmitted through, or reflected from said sample, said radiation including at least three discrete components selected from a spectral range so that at least one of said components is subjected to said optical interference, absorption or scatter and so that said components are transmitted through, or reflected from said sample by respectively different amounts;

(b) measuring the transmittance or reflectance of said sample for each of said components to derive respective measured values;

(c) correlating said measured values of transmittance or reflectance with different known values of transmittance or reflectance, said different known values representing or relating to either different values of a property of a known material, or different values which are characteristic of different known materials;

(d) selecting the known values having an optimum correlation with said measured values, the selected known values representing the property, or the identity of the sample which is sensed or to be determined.

The latter method provides distinct advantages over the system disclosed in US-A-4555767 (in which the "selection" of radiation components is absent). For example, far less radiation components (e.g. wavelengths) are required in order to obtain an equally accurate result. This not only reduces computing time, but it also means that more simple, robust and cheaper instrumentation can be used, especially in industrial environments. The invention can also be more broadly applied, e.g. to make transmittance as well as reflectance measurements, particularly in applications where absorption effects are present instead of, or as well as interference effects. Moreover the invention is particularly valuable in thickness measurement in the intermediate thickness range where neither absorption nor interference effects provide an adequate basis for measurement. For example, in spectral regions where weak absorption or interference effects are present, if conventional equipment were used to measure film thickness with a beam of radiation having a wavelength of, e.g. 3.4 microns, the measurement resolution might be 0.1 microns. However, the invention can be embodied to easily improve the resolution to 0.02 microns or better.

The selection of the radiation components may depend on the optical effect of the sample. Preferably, in the case of interference, the spectral properties of the radiation components are irregularly spaced. For example, where the radiation components are wavelengths (or narrow wavebands having a mean wavelength), the wavenumber spacing is preferably irregular. Otherwise, the choice of wavelengths is relatively uncritical. The wavelengths are also preferably chosen to extend over about 1 cycle of the optical interference pattern for optical paths at the low end of the measuring range. Irregular spacing between the radiation components is preferred where interference effects are encountered, whether such effects are dominant or not, or in cases where both interference and absorption effects are present, e.g. in an intermediate range of film thickness measurements. Suitable sets of spacings may be given by so-called "minimum redundancy linear sequences" sometimes called Golomb rulers. Examples are:

for 3 wavelengths, spacings of $\frac{1}{3}$, $\frac{2}{3}$
for 4 wavelengths, spacings of 1/6, $\frac{1}{3}$, $\frac{1}{2}$
for 5 wavelengths, spacings of 1/9, $\frac{1}{3}$, $\frac{1}{3}$, 2/9
of the span of wavenumbers in the sequence.

In the case of absorption measurements, it is preferred that at least two of the components are located at, or near an absorption band or edge for the sample so that at least three of the components are relatively and differently absorbed by the sample. Where the sample exhibits a generally known absorption band, the components are preferably selected so that they include several on both the long and short wavelength sides of the absorption band maximum (some of which components may be outside the band as long as at least two of the components are within the band). However, where the sample exhibits a plurality of absorption regions, at least two of the components may be within respective regions so that again at least three of the components are relatively and differently absorbed.

In the case of scatter, the radiation components may be different wavelengths which are preferably selected so that at least three of the wavelengths are scattered by different amounts by the sample. The components could alternatively have different angles of incidence in order to produce the same effect.

The "known" values, which are correlated with the "measured" values, may be derived by either an analog, or a digital technique.

In the analog technique, the electromagnetic radiation is transmitted through, or reflected from either a material similar to the sample and having different known magnitudes of the property to be sensed or determined, or different known materials having different known magnitudes of the property to be sensed or determined. For example, in determining the thickness of a sample film, films made of similar material and having different known thicknesses can be used to provide known values of transmittance or reflectance. These known values may be provided as the instrument is used, e.g. by scanning across a wedge of the sample material in the case of thickness measurements. Alternatively, they may be provided before the instrument is used, in which case they can be stored, as digital values, in the memory of a computer which is used to correlate the measured values with the known values in order to provide optimum correlation data from which the property or identity of the sample can be determined. An instrument embodying the invention may include a computer programmed to operate in a "learning" mode, in which the instrument is "taught" the appropriate known values and computational techniques to provide the required results (this also applies where the known values are derived in the digital technique mentioned below).

In the digital technique, the known values are model values which are derived by applying, to a mathematical model or models, (i) known values relating to the properties of the radiation components, and (ii) different magnitudes of the property to be sensed or determined. Different models may be employed to provide expected values of transmittance or reflectance, the choice of model depending on how the invention is used in practice. For example, where a property, such as film thickness, is not likely to vary widely and/or where measurements are not likely to be swamped by dominant interference effects, a simple model could be employed which depends solely on absorption effects. Similarly, where the property does not vary widely and/or measurements are not likely to be swamped by dominant absorption effects, a simple model could be employed which depends solely on interference effects. However, there are often situations where the property to be determined is likely to vary by large amounts, or in some unpredictable way and where either interference, or absorption effects could alternately dominate thereby affecting the accuracy of measurement.

In accordance with another aspect of the invention, which may be used either with, or without the selection of radiation components mentioned above, the latter problem is solved by the use of a model or models which take account of absorption and interference and/or scatter. For example, more than one model may be used to provide sets of expected values of transmittance or reflectance that respectively take account of absorption, interference and scatter and to provide corresponding measurement values. The set of values with the optimum correlation can then be selected. However, it is preferable to employ a model which simultaneously takes account of e.g. absorption and interference effects in providing the expected values of transmittance or reflectance. This provides more accurate model values and facilitates the step of determining optimum correlation with the measured values and automatically eliminates errors due to dominant interference or absorption effects. This provides significant advantages over prior art techniques where (a) either absorption gauges, or interference gauges are separately used, (b) attempts are made to supress interference effects when using absorption measuring techniques, or to supress absorption effects when using interference measuring techniques, and (c) where the choice of a parameter such as radiation wavelength is a problem (due to measuring an unknown property or an unknown material).

The correlation between the measured values and respective known values can be automatically determined by computing means, such as a microprocessor. In the digital technique, the computing means is programmed with the appropriate model or models for deriving the expected values of transmittance or reflectance when data is applied to the model or models which represents values of the properties of the radiation components and of the different known magnitudes which relate to the property or to the identity of the sample to be sensed or determined. Parameters which affect the optical properties of the sample may also be applied to the model or models, e.g. parameters such as temperature and pressure. The computing means enables the unknown property or identity of the sample to be rapidly determined or sensed and this is important in the manufacture of materials by continuous processes where rapid accurate sampling is desirable. Preferred embodiments of the invention can be used advantageously to provide automatic control in such continuous industrial processes where the property or identity of the sample needs to be accurately, rapidly and continuously or periodically monitored.

Where interference effects are present, correlation coefficients computed between measured and model values show oscillatory characteristics (FIG. 2) with a maximum amplitude where the measured and model values correspond. Another aspect of the invention improves accuracy of identification of the maximum correlation coefficient. This aspect of the invention may, or may not be employed together with the selection of radiation components and the use of a model or models taking account of absorption and interference (as explained above).

More particularly, this aspect of the invention provides a method wherein correlation coefficients are computed between the measured values and known values derived from a mathematical model or models, the optimum correlation between the measured and model values being a zero correlation value in the correlation between measured values and model values derived from a differential function of the model or models to which the known values relating to the properties of the radiation components, and different magnitudes of the property to be sensed or determined are applied.

A reduction in computing time can be achieved by reducing the range of known values which are correlated with the measured values. This is particularly advantageous when the known values are model values derived by applying a range of known magnitudes to a model in the digital technique. For example, a range of regularly spaced thickness values could be limited to encompass an estimated thickness value where the thickness of a sample is only likely to vary by a small amount about a known mean value. In such cases, the range is limited to the values on each side of a predicted mean value. However, where the property or identity of the sample is completely unknown or is likely to have largely unpredictable variations, the problem arises of limiting the range of values on either side of an unknown value. According to one embodiment of the invention, the range of known magnitudes is limited with regard to the measured values of transmittance or reflectance, since these measured values provide a first estimation of the unknown value to be determined or sensed. The range of known magnitudes may be automatically and sequentially limited depending on the selection of known values providing the highest correlation coefficients. In this way, the range of magnitudes will shift with changes in the unknown property or identity of the sample.

Whilst computing time can be reduced in the invention by reducing the number of radiation components used in making the transmittance and reflection measurements, this can sometimes have the effect of obscuring the maximum correlation coefficient. For example, a multiplicity of correlation coefficient peaks having apparently similar values will be obtained when using a few radiation components.

According to another aspect of the invention, which may be independent of the previous aspects of the invention mentioned above, the latter problem may be solved and a further and massive cut may be made in computing time by a method for sensing or determining one or more properties of the sample, the method comprising the steps of:

(a) causing electromagnetic radiation to be transmitted through, or reflected from said sample, said radiation including two or more groups of radiation components, each group including at least three components having respectively different properties;

(b) measuring the transmittance or reflectance of said sample for each of said radiation components to derive respective measured values;

(c) deriving known values of transmittance or reflectance by applying to a mathematical model or models (i) known values relating to the properties of the radiation components, and (ii) different magnitudes of the property to be sensed or determined;

(d) computing correlation coefficients between said measured values and said model values for said two or more groups of said radiation components having relatively different properties;

(e) determining correlation coefficients for each group of said radiation components over a limited range of known magnitudes;

(f) deriving the highest correlation coefficients from the latter step (e) and using them to compute the magnitudes at which peaks occur in the correlation coefficients for each of said group; and (g) selecting the model values at the known magnitudes where the correlation coefficient peaks are coincident, or most nearly coincident.

The radiation components of each group may be different or there may be some components common to each group, as long as the groups differ. For example, in the case of two groups, only four components may be used with two common components in each group. However, more than four components would normally be used.

Where there is more than one magnitude at which the correlation coefficient peaks are coincident, or most nearly coincident, the further steps are carried out of limiting the range of known magnitudes to those providing the coincident or most nearly coincident peaks and selecting, from the limited range, the model values at the known magnitude at which the correlation coefficients are highest.

Generally speaking, the choice of transmittance or reflectance measurements will depend on the nature of the sample, e.g. transmission being used in the case of a sample which transmits radiation, and reflection being used with a sample with limited or zero transmission which reflects or scatters radiation. In the case of reflection, the sample may be a granular material on which a substance is sorbed, the amount of the sorbed substance affecting the optical properties of the sample, or analogously a textile yarn or thread which is coated with a substance. In the case of scattering, the sample may be a film containing a pigment, the amount of which affects the way in which the radiation is scattered.

The spectral properties of the components of radiation may differ in respect of their wavelengths, angles of incidence, polarisations, or possibly combinations thereof. The choice will depend on the property to be sensed or determined. For example, the radiation components may have respectively different wavelengths or mean wavelengths in the case of thickness determination, the bandwidth of each component being less than the difference between adjacent wavelengths. In the case of optical anisotropy, the components may have different wavelengths, different polarisations or different angles of incidence, or any combination thereof.

It is not necessary for the transmittance or reflectance to be restricted to the specular case for the invention to operate. Diffuse transmittance (for example of light through a sample of paper) and diffuse reflectance (for example from a powder) could be measured. In such a case, known values (used in either the analog or digital technique) represent the way in which the light is transmitted, reflected or scattered by the sample.

The invention further provides apparatus for performing the methods in accordance with the different aspects of the invention mentioned above, such apparatus being defined in the appended claims. Such apparatus preferably comprises computing means which automatically determines the optimum correlation between the measured and known values. In the analog technique, the known values may be stored or provided whilst the apparatus is in use as mentioned above. In the digital technique, the computing means is programmed with the appropriate model or models and is supplied with the appropriate data to enable the model values to be computed. The computing means may be suitably provided with a keyboard to provide a data input. The keyboard could be used to enter the data relating to the known values and/or the computing means preferably stores tables of values from which sets of values can be selected to suit the particular application. With the digital technique, different models may also be stored in the computing means which are either manually, or automatically selected depending on either predictions of unknown properties or identities, or first estimations derived from initial transmittance or reflectance measurements.

Embodiments of the invention will now be described with reference to the accompanying drawings, in which:

FIG. 1 is a schematic graph showing the percentage of transmittance and reflectance of a sample of a transparent organic film over a range of wavelengths in microns.

FIG. 2 is a schematic graph showing the variation in the correlation coefficient between sets of measured transmittances of a polymer film with an optical thickness of about 10 microns and sets of model transmittances over a range of optical thicknesses from 0 to 20 microns, the model values being based on the transmittances of radiation components having various wavelengths between 1.7 and 2.3 microns.

FIG. 3 is a schematic graph showing the variation in the correlation coefficient between sets of measured transmittances of a polymer film with an optical thickness of about 10 microns and sets of model transmittances over a range of optical thicknesses from 0 to 20 microns, the model values being based on the transmittances of radiation components having various wavelengths between 1.9 and 2.1. microns.

FIG. 4 schematically illustrates optical apparatus according to one embodiment of the invention for making transmission measurements.

FIG. 5 schematically illustrates optical apparatus, according to another embodiment of the invention, for making reflection measurements.

FIG. 6 is a schematic graph showing the variation in correlation coefficient between sets of measured transmittances of a film with an optical thickness of about 10 microns and sets of model transmittances over an optical thickness range from 0 to 20 microns, the model values being based on the transmittances of radiation components in two groups of wavelengths, having approximate mean values of 2.0 microns and 1.6 microns. Applications of various embodiments of this invention may include the following:

(i) Measurement of the thickness and determination of the composition of films, coatings and layers.

(ii) Measurement of the thickness and determination of the composition of one or more components of a co-extruded film, laminate or layered structure.

(iii) Determination of the structure of a co-extruded film, laminate or layered structure.

(iv) Measurement of the quantity of a material sorbed onto the surface of granules, particles, grains or fibres of another material, for example, the moisture content of powered coal or polymer granules. Such a measurement will generally be carried out by reflection, specular light being reflected by randomly oriented surfaces of the granules, particles, grains or fibres.

(v) Measurement of the quantity of one material distributed in another material or the composition or other properties of a material. Such a measurement will usually, although not invariably, be carried out by transmission and will apply to materials in solid, liquid or gaseous phase. Examples are dielectric particles such as Titanium Dioxide in a solid polymer, water in oil and hydrocarbon vapours in air. (These examples are of single phase materials but this is not a necessary restriction: mixed phase materials such as emulsions and aerosols can also be measured). In the case of measuring the quantity of distributed material, it is necessary that the several constituents of the material differ from one another in at least one of their optical properties in order that they may be distinguished. Such a property may include refractive index, absorption coefficient, scatter coefficient or optical anisotropy. For certain materials, especially gases, the optical properties of the material are affected by its temperature and pressure as well as its composition and these properties may also be determined by incorporating them into a model that describes the theoretical transmittances or reflectances. Especially when measuring properties of gases, if spectral absorption effects are taken into account, the spectral absorption characteristics of the material will be complex and have a bandwidth or bandwidths much narrower than those of the optical filter means used in the measurement and it will be necessary for the computation of theoretical transmittance or reflectance to integrate the influence of these narrow spectral features across the bandwidth of the optical filter means, instead of treating the filter as a way of producing monochromatic radiation.

(vi) Measurement of the optical anisotropy of films, coatings and layers. This may be effected either by optical path measurements using beams of radiation at two or more differing orientations with respect to the sample to be measured, or by using beams of radiation of differing polarisations at a common angle or by using beams at wavelengths which exhibit differential sensitivities to optical anisotropy. For example, polymer films are stretched during production so as to enhance their strength and other mechanical qualities. Such stretching leads to the film being optically anisotropic and exhibiting three different refractive indices for radiation propagated in three orthogonal directions, one normal to the film and the other two in the plane of the film. By comparing measurements of the optical path for beams of electromagnetic radiation traversing the film in different orientations, the anisotropy of the film can be estimated and the stretching process can be controlled. In the manufacture of other items, such as substrates for semiconductors manufacture and certain optical components, anisotropy is an undesired characteristic. In this case, measurements of the optical paths by beams of electromagnetic radiation traversing the film in different orientations can be used to verify that the anisotropy does not exceed acceptable limits.

By way of example, embodiments of the invention will now be described which are concerned with the measurement of thickness. However, it will be understood that the principles involved can be adapted for the determination of other properties such as the composition and structure of a sample; the optical anisotropy of a sample; and the moisture content of relatively impermeable granular or powdered materials such as crushed coal or coke and metallic ores and metals; etc.

Hereinafter the term 'light' will be used in place of 'electromagnetic radiation', it being understood that as used, 'light' does not imply a restriction to the part of the electromagnetic spectrum to which the eye is sensitive. Similarly no such restriction is implied by use of the word 'optical'. Further, in all references to 'detector', unless otherwise stated it will be understood that this is a radiation responsive detector which generates a signal related to the intensity of the electromagnetic radiation incident upon it.

In the following explanation frequent reference will be made to computation of covariance and correlation coefficient between groups of signals, and of the variance of a group of signals. Whilst these terms are well known in the statistical analysis of data (see for example "Statistics and computer Methods in Basic" by J. D. Lee and T. D. Lee, published by Van Nostrand Reinhold Company Ltd in 1982) it will be helpful to define them here.

Consider a situation in which it is supposed that there is an approximately linear relationship between two groups of values x and y where i is an integer reference in the range 1 to k.

Then the variance of the x values is given by $$v_x = \frac{\Sigma(x_i - \bar{x})^2}{k} \quad (1)$$

where $\bar{x}$ represents the mean of the x values, given by $$\bar{x} = \frac{\Sigma x_i}{k} \quad (2)$$

($\Sigma$ represents summation over all values of i in the usual way).

Similarly the variance of the y values is given by $$\sqrt{v_y} = \frac{\Sigma(y_i - \bar{y})^2}{k} \quad (3)$$

$$\text{where } \bar{y} = \frac{\Sigma M_i}{k} \quad (4)$$

The covariance of the x and y values is given by $$Cxy = \frac{\Sigma(x_i - \bar{x})(y_i - \bar{y})}{k} \quad (5)$$

The correlation coefficient r is defined by $$r = \frac{C_{xy}}{(\sqrt{V_x} \cdot \sqrt{V_y})^2} \quad (6)$$

It will be seen that if equations (5), (1) and and (3) are substituted into equation (6) then k, the number of values in each of the groups will cancel out. It is therefore useful to define sums of squares and products of deviations as follows $$W_x = \Sigma(X_i - \overline{X})^2 \quad (7)$$

$$W_y = \Sigma(y_i - \overline{y})^2 \quad (8)$$

$$d_{xy} = \Sigma(X_i - \overline{X})(Y_i - \overline{Y}) \quad (9)$$

It may be convenient to describe these as variances and covariance respectively. Where any confusion may arise it will be clarified by referring to equations (1), (3) and (5) as giving normalised variances and covariance respectively and equations (7), (8) and (9) as giving un-normalised variances and covariance respectively. Use of the un-normalised values will often be preferable as a means of reducing the amount of computation that is required.

FIG. 1 schematically shows the transmission and reflection spectra of a thin transparent film of an organic material. Infrared absorption bands are evident in the transmission spectrum at about 2.3 and 3.4 microns, although at 2.3 microns the absorption is largely masked by the optical interference effect. In the reflection spectrum the weaker band at 2.3 microns is not apparent at all and the stronger band at 3.4 microns is scarcely distinguishable from optical interference. Both transmission and reflection spectra are dominated by optical interference, producing the familiar modulation pattern often described as a 'channel spectrum'.

It will be noted that in the regions away from the absorption bands, the transmission maxima coincide with the reflection minima and vice versa. FIG. 1 depicts a spectrum in which the abscissa is shown as linear in wavelength, and the spacing of the interference maxima increases with wavelength. Had the spectrum of FIG. 1 been plotted with an abscissa linear in wavenumber then the sinusoidal modulation would appear to have an almost constant period.

It will also be noted that the contrast of the optical interference spectrum diminishes at shorter wavelengths. There are two probable reasons for this: firstly, at shorter wavelengths the maxima become progressively closer together and the spectrometer used to generate the spectrum may have inadequate resolving power and secondly, non-flatness or non-parallelism of the surfaces of the film becomes a progressively greater fraction of the wavelength as we move to shorter wavelengths and the resulting phase variations attenuate the fringe contrast.

The transmission maxima (and reflection minima) occur when twice the optical thickness of the film is equal to an integer number of wavelengths $$2ng = j\lambda \quad (10)$$

where n is the refractive index, and g the film, thickness, j is a positive integer and $\lambda$ the wavelength.

To a first approximation, the transmission of the film at a wavelength (away from the absorption bands) is given by:

$$T(\lambda) = 1 - \alpha + \alpha \cos(4\pi ng/\lambda) \quad (11)$$

and the reflection from the film by:

$$R(\lambda) = \alpha - \alpha \cos(4\pi ng/\lambda) \quad (12)$$

Whilst these equations are oversimplifications of the situation, they are helpful in understanding the digital embodiment of the invention: more accurate (and complex) equations will be discussed later.

With conventional instrumentation (i.e. which does not employ a correlation technique), the thickness of the film whose spectrum is illustrated in FIG. 1 could have been determined by measuring its transmittance at about 3.4 microns (the absorption waveband) and at a reference wavelength or wavelengths, such as 3.2 microns and computing its thickness from the ratio of these transmittances. Such a measurement would be affected by optical interference errors.

The mode of operation of the preferred embodiment of the present invention is quite different: the transmittance of the film is measured at a number of wavelengths—at least three and commonly between 8 and 12. These wavelengths represent components of radiation which are selected in accordance with the first aspect of the invention mentioned above.

Trial (known) values of thickness over a predetermined range are applied to a model in order to calculate model values of transmittance (or reflectance) of the film for each of the measurement wavelengths.

Using the mathematical relationships previously explained, the correlation coefficient between the set of measured transmittance (or reflectance) values and the set of theoretical transmittance (or reflectance) values is computed for each trial value. If necessary new trial values are generated re-iteratively until a value of trial thickness is found which yields the highest possible correlation coefficient for any trial value in the possible range. This trial value is taken to be the actual thickness value.

Several different methods of determining trial values will be taught, as will several different methods of finding the trial thickness that yields the highest possible correlation coefficient.

Other methods will be taught, whereby the set of measurement wavelengths is divided into groups and the correlation coefficient calculated for each trial value for each group. New trial values are generated re-iteratively until a trial value is determined which leads to a set of sufficiently high correlation coefficients for all the groups.

In the case of thickness measurements with a sample which is not optically flat enough to provide accurate results from an interference technique, the sample may not exhibit any significant absorption which would enable measurements to be made by an absorption technique. However, the invention could be used with known values relating to interference to provide an accurate result. Where absorption is present, the selected wavelengths may be within absorption bands. As mentioned below, it is possible to identify a material from a range of possibilities by including absorption bands in the range of wavelengths selected and that it is also possible to extend the thickness range over which the method will operate by including absorption bands.

Unlike some existing methods for optical path and optical thickness determination which utilise interference effects, a method embodying the invention does not require measurements across a continuous wavelength region of the spectrum, nor does it require the wavelength positions of optical interference maxima or minima to be measured with great precision. In addition, it is capable of operation on materials whose surface flatness and parallelism are too variable to permit the use of known interference techniques.

When using a method embodying the invention to measure the optical thickness of coatings, or of laminates containing several components of differing optical properties, within the ranges of trial values (for each component) several trial values may produce sufficiently high correlation values as to justify their selection as the actual thickness. Methods for identifying and suppressing false trial values which may exhibit high correlations and methods for determining which of several trial values is correct are taught.

An important characteristic of optical absorption gauging apparatus according to the prior art is that the measurement is based on the calculation of a ratio, or ratios of signal intensities, so that the apparatus need only measure relative intensities. Embodiments of the invention share this desirable characteristic, for the correlation formula used (6) is likewise unaffected by the absolute values of the transmittance or reflectance signals, either measured or calculated.

Further, the correlation coefficient is unaffected by the mean value within the set of data points so that when computing correlation coefficients, constant terms may be added to or substracted from all the measured or all the calculated signals, or both, if this simplifies the computation.

It will be taught that in some situations it may be beneficial to compute correlations of both reflected and transmitted signals. It will also be taught that, unlike optical absorption gauging, the direction through the material in which transmission measurements are made may influence the result.

One method of embodying the invention is to spread the set of measuring wavebands out over a wide range of spectral bandwidth and to correlate the measured and calculated values as a single group. In this method it is important to avoid using measuring wavebands regularly spaced in wavenumber where interference is present. The simplest method of computing the optical path in this situation is to correlate the measured set of transmittance or reflectance values with the theoretical set for all trial values within the defined range, at an interval of trial value which is commensurate with the desired accuracy. This may be a relatively slow procedure but in laboratory measurements speed is not usually necessary. In the case of on-line measurements it is usual for the rate of change of optical path to be limited by the nature of the production process and once a value has been determined it may be possible to reduce the range to a narrow one about the determined value and this will speed up subsequent measurements.

Such a method may be described as a 'brute force' method and more subtle methods exist which utilise the fact that the variation of correlation coefficient as a function of trial value (for a given set of measurement values) is a reasonably predictable function with known characteristics.

To illustrate this FIG. 2 shows a typical variation in correlation coefficient as a function of trial optical thickness, for a set of measurements of the transmission of a polymer film of optical thickness of about 10 microns. For typical polymers there may be a weak absorption band at around 1.7 microns, but for polymer films in this thickness region the absorption will be negligible and interference effects will dominate. The six measurement wavebands are distributed over the spectral band between 1.3 and 2 microns, the wavebands are narrow in comparison with the spectral band and the mean wavenumbers of the wavebands are irregularly spaced.

FIG. 3 shows a corresponding variation for the same film, in which the six narrow measurement wavebands have been restricted to a much narrower spectral band between 1.7 and 2.3 microns. In this case, the mean wavenumbers need not be irregularly spaced. The wavebands are employed in two groups with a correlation technique (explained later) wherein correlation coefficients are computed between measured values and known values for the two groups of wavebands.

It will be seen that FIG. 2 the correlation coefficient shows a maximum value when the trial optical thickness value is equal to the actual value and shows oscillatory characteristics for trial values above and below. The period of the oscillation is about 1.0 microns, which is half the average wavelength used in the measurement. In FIG. 3 the correlation coefficient again shows a maximum when the trial value is equal to the actual value. However, the oscillation is more regular and the peaks of correlation coefficient which are regularly spaced at 1.0 micron, (which is half the average wavelength used in the measurement) decay much more slowly as trial value moves away from actual value. Thus, provided that the spectral bandwidth is not too great, once the trial value position of one peak of correlation coefficient is known, the trial value positions of adjacent correlation coefficient peaks can be predicted. If the measurements have been made with sufficient precision then it may be safely asserted that the trial value position of the highest correlation coefficient peak will be the desired actual value. However, if the spectral bandwidth is sufficiently restricted to yield regularly spaced correlation peaks then the reduction in height of the peaks to either side of the actual value may be less than height variations produced by measurement, computation or other errors and the identification of the actual value becomes uncertain. A method of resolving this uncertainty will be taught later.

Accurate identification of the trial value positions of the correlation peaks as plotted in FIGS. 2 and 3 can be achieved by the following technique.

When correlation coefficient is plotted against trial value of optical path, a correlation coefficient peak implies that the differential of correlation coefficient with respect to trial optical path shall be zero at the trial value corresponding to the peak, positive at a trial value just less than that of the peak and negative at a value just greater. It may be shown that instead of identifying peaks in the correlation coefficient between measured and theoretical values as a function of trial value, it is equivalent to identify zeros in the correlation coefficient between measured values and the values relating to the differential (with respect to trial value) of the equation which describes the theoretical transmittance or reflectance as a function of trial value. This technique may be used with or without the selection of radiation components as mentioned above and below. For the zeros in the correlation between measured values and differential theoretical values to correspond to maxima and not minima in the correlation between measured values and non-differential theoretical values, it is necessary to select the zeros where the correlation coefficient moves from positive to negative as the trial value is increased through the peak region. Use of this technique provides a significant improvement in the efficiency of the method. This is especially so when the differential of the theoretical equation can be calculated as easily as the theoretical value itself, which is usually the case if a spectral region with negligible absorption is chosen for the measurement.

Referring to FIG. 4, which shows apparatus operating by transmission through a sample according to an embodiment of this invention, a number of light beams including three or more of narrow spectral bandwidth centered on different and known wavelengths are generated by source, 1, and directed by first optical directing means, 2, into sample zone, 3, so that they impinge upon sample, 4, at a defined angle of incidence. That fraction of each of said beams which is transmitted by sample, 4, is then directed by second optical directing means, 5, onto detector means, 6. The signals produced by detector means, 6, which represent the several intensities of those fractions of each of said beams which is transmitted by sample, 4, are amplified and demodulated if necessary by signal processing means, 7, and transmitted to computing means, 8, which compute the optical path or paths within sample, 4, by means and methods which will be described later.

Referring to FIG. 5, which shows apparatus operating by reflection from a sample according to an embodiment of this invention, a number of light beams including three or more of narrow spectral bandwidth centered on different and known wavelengths are generated by source, 1, and directed by first optical directing means, 2, into sample zone, 3, so that they impinge upon sample, 4, at a defined angle of incidence. That fraction of each of said beams which is reflected by sample, 4, is then directed by second optical directing means, 5, onto detector means, 6, which represent the several intensities of those fractions of each of said beams which is reflected by sample, 4, are amplified and demodulated if necessary by signal processing means, 7, and transmitted to computing means, 8, which compute the optical path or paths within sample, 4, by means and methods which will be described later.

Referring to FIGS. 4 and 5, range defining means, 9, for defining a range within which said optical path is known to lie may be provided externally as shown or may form an additional function of parts of the apparatus as described above.

The choice of spectral band over which measurements may be made is a function of the optical properties of the sample and it is necessary that optical interference, scatter or absorption effects shall operate at some wavelengths within the spectral band so that the transmittance or reflectance of the sample shall be relatively different for at least three radiation components.

The choice is further influenced by the availability of elements from which a measuring system can be assembled, such as radiation sources, wavelength determining elements such as filters, radiation detectors and optical elements required to direct the radiation components. Such elements must be of appropriate robustness and reliability to suit the environment in which they are used and preferably both easy and safe to use.

For example, in measuring the thickness of certain polymer films by absorption, strong absorption features occur in the ultra-violet and mid-infrared (3-12 microns), and weaker bands in the near infrared (1-3 microns). The latter spectral band is commonly chosen from measurement because, whilst its absorption features are less favourable, robust and reliable elements from which to build the system are available, unlike the mid-infrared, and they present no safety hazard, which ultra-violet sources may do.

Within the spectral band, the selection of the spectral characteristics of the radiation components depends on the relative contributions of optical interference, scattering or absorption towards making the transmittances or reflectances of the sample relatively different for at least three of the several radiation components.

According to one aspect of the invention a minimum number of radiation components are used thereby simplifying the apparatus and minimizing the computing effort needed to obtain a result.

When optical interference is present, either as the predominant contribution or as one which would cause serious errors to a model based on absorption or scatter, then the choice of spectral components must take into account optical interference effects.

When choosing spectral components it is often convenient to select spectrally narrow bands for the radiation components so that the model or models (in the digital technique) can be simplified by permitting radiation over the finite spectral bandwidth of each radiation component to be treated as monochromatic.

Where optical interference predominates the in order for such interference to affect the intensities of the components, the coherence length of the radiation components must be greater than the optical thickness of the sample.

Such a condition must be satisfied throughout the range of anticipated sample thickness.

The fewer the radiation components selected from the spectral range, the more critical their selection. Band selection results in correlation coefficient peaks being observed at many trial values additional to the correct one.

When optical interference is present, irregular spacing in wavenumber gives much better results than regular spacing.

A particularly effective method of spacing, permitting good results for a minimum number of radiation components is to space according to so-called "minimum redundancy linear sequences" sometimes described as "Golomb rulers".

Examples of such sequences are:
for 3 wavelengths, spacings of ⅓, ⅔
for 4 wavelengths, spacings of 1/6, ½, ⅓
for 5 wavelengths, spacings of 1/9, ⅓, ⅓, 2/9
of the span of wavenumbers in the sequence.

Further examples for higher numbers of wavelengths may be determined by reference to IEE Transactions on Antennas and Propogation, Vol. AP-16, No. 2, Mar. 1968, pages 172-175 in an article by A. T. Moffett, titled "Minimum Redundancy Linear Arrays".

When optical interference is present and radiation components are correlated in two or more groups (as mentioned above and below), there is no need for such irregular spacing since the aim is to produce regularly spaced correlation peaks against trial value and to look for coincidences between arrays of such peaks, assuming known spacings and the positions of just one peak in each group.

The wavenumber spacing of components within each group should extend over at least a half, and preferably a whole cycle of the interference pattern for the lower end of the optical thickness range of the sample.

Since the spacing of the correlation peaks when plotted against trial value is inversely proportional to the mean wavenumber of the group, the occurrence of coincidences between groups can be regulated by choice of mean wavelengths for the groups.

Where absorption is predominant, the criteria for choice of wavebands are somewhat different. Suitably, there are at least three radiation components with relatively different responses to the parameter to be measured, unlike conventional absorption gauging techniques where two will suffice.

Narrow spectral regions may be chosen with reference to an absorption band or edge, so as to provide relatively different absorptions; or one or more regions free of absorption can be selected plus two or more at different absorptions with respect to one absorption band; or even two (or more) absorption bands can be employed if they exist within the spectral band available.

An alternative is to use three or more radiation components of similar mean wavelength but differing bandwidth. Such a method may lead to difficulties in generating the model values for correlation, so that they would need to be determined by measurement on known samples or by a simplified empirical model.

When scatter is predominant, the criteria for choice of wavebands are similar to those for absorption so that in general scattering processes in the sample will exhibit a relatively slow variation with wavelength and hence relatively broad bandpass filters may suffice. Again at least three relatively different responses to the parameter to be measured are required.

When absorption and optical interference co-exist an efficient selection of wavelengths is one which satisfies both the criteria of irregular spacing and of relatively different responses as described above.

Unlike the case where optical interference is present, the absorption and scattering cases are not characterised by false correlation peaks and relatively small numbers of wavelengths will suffice.

The improvement in moving from the minimum of 3 components to (say) 5 is that good results may be obtained with a poorer measurement signal to noise ratio and that the result may be less affected by parameters other than that being measured.

It will also be obvious to persons skilled in the art that when a spectrally broadband source is used, the precise location of the optical filter means in the light path from source to detector is not critical. Indeed, it may be more convenient to illuminate the sample with a broadband source and only select the spectrally different beams after the light has been transmitted or reflected by the sample.

The first and second optical directing means are optical elements, or combinations thereof that are well known in the prior art, including lenses, mirrors, prisms optical fibres etcetera. In some cases one optical element or combination may be made to serve as first and second optical directing means, and in the case of some systems using a laser or lasers as source, the optical systems of the laser or lasers in effect may provide either the first, or the first and second optical directing means.

The detector means may include one or more detectors. If the number of detectors is less than the number of light beams, then some means of presenting two or more beams to at least one of the detectors must be utilised. Such means could include sequential presentation (for example, by means of a rotating filter wheel) or the modulation of each beam at a different frequency, with a corresponding demodulation of the detector signal. In the event of sequential presentation being used, all beams must be presented in a time which is so short that the optical path within the sample will not have changed during the sequence. Especially for on-line measurement, this is a fairly demanding requirement and apparatus permitting simultaneous measurement of the beams may be preferred.

Where a multiplicity of detectors is adopted it may prove beneficial to provide for adjustment or correction for the relative sensitivities of the detectors for example, after measuring the detector signals in the absence of a sample, or in the presence of a known sample or both.

The apparatus may be designed to function with a wide range of types of detector. The choice of detector will depend upon the spectral region over which the apparatus is to operate, upon the desired response speed of the measurement and will present few difficulties to those skilled in the art. Detectors which could be used include photomultiplier tubes, silicon or germanium photodiodes or arrays thereof such as charge-coupled-devices, photoconductive and photovoltaic semiconductors, and thermal detectors such as thermocouples or pyroelectric detectors or arrays thereof.

The signal processing means may use known electronic means to amplify the signal or signals from the detector or detectors and to demodulate the signal or signals so as to produce the set of signals which represent the transmission or reflection of the sample for each of the light beams used. If adjustment or correction for the relative sensitivities of the detectors is required it may be applied at this stage or it may be applied as part of the subsequent computing means.

The sequence of operations by which the computing means measures the optical path or paths within the sample will be described later. Commonly the computing means will use known electronic and microprocessor technology to convert the set of signals representing the transmission or reflection of the sample from analogue to digital format, to effect the operating sequence and to provide output or control signals, as a result of this sequence. Certain parts of the sequence such as the computation of sines and cosines may utilise previously calculated values stored in a look up table as is known in the art of computing. Especially in the case of an on-line measurement where a rapid response may be required, more than one micro-processor may be required. It is anticipated that optical computing means will shortly become available and it is quite probable that by using such means, the signals from detection means, through signal processing means and computing means will be partly or entirely in the form of light signals rather than electrical signals.

Nonetheless, it will be convenient here to describe the sequence of operations in terms of known electronic signal processing and computation but this is by way of example and not a limitation of the scope of this invention.

This invention includes several alternative range defining means. For many measuring instruments the design of the instrument implicitly defines the overall measuring range. For example, in the case of a film thickness gauge operating by known optical absorption means, the maximum film thickness that can be measured will be set by the film thickness through which the transmission is just sufficient to produce an acceptable signal to noise ratio in the measurement.

The spectral bandwidths and spectral differences between the beams will be determined with reference to the overall measurement range. Further, the calculations needed to determine the optical path are re-iterative in nature and if the possible range of optical path can be reduced then the average time needed to effect the calculations can also be reduced.

One range defining means is to introduce the maximum and minimum optical path values into the program or sequence of operations needed to effect the calculation. A second range defining means is to manually enter the maximum and minimum optical path values into the computing means by known techniques such as a keyboard or thumbwheel switches or calibrated potentiometers.

A further range defining means is an optical absorption gauge constructed according to the known prior art. Whilst the measurement produced by such an instrument may be affected by optical interference errors, it can be relied upon to provide an approximate value about which a restricted range can be defined. To persons skilled in the art it will be apparent that in the embodiments of the invention as described herein which relate to absorption, there exist all of the components of an optical absorption gauge, provided that the spectrum of one of the beams includes wavelengths located on or near an absorption band for the sample material. This combination of known optical absorption gauging with the correlation technique herein described is employed by an embodiment of this invention. This combination has two important characteristics: firstly the optical absorption measurement can provide an approximate value, from which a range may be defined for the correlation measurement and secondly, in the event of the sample surfaces being insufficiently flat and parallel to generate optical interference effects then a measurement, possibly of lower accuracy, can still be obtained by the optical absorption gauging means. In general the optical absorption gauging method will permit the operating range of the instrument to be extended to thicker samples using longer optical paths.

Other range defining means include known gauging apparatus using alternative technologies such as nuclear gauging, microwave gauging and capacitance measurement, as well as transducers using mechanical or electromechanical means to determine the thickness.

Frequently, when measuring instruments are used on a production process or line, characteristics of the production process or line will limit the rate at which the optical path can change. In such situations, once an optical path value has been determined, an appropriate range for the next measurement may be set by applying limits above and below the determined value, separated by a spacing determined by the time delay between measurements and the speed at which the process can change. The new optical path value will in turn permit limits to be set for the next optical path value and so on. It is desirable for such a procedure to incorporate some means of automatically widening the range and re-starting in the event that for some reason a correct value cannot be securely identified within the limited range.

Examples of the sequence of operations required of the computing means will now be described with reference to Tables 1 to 3. In these tables are shown the constants required for the computing sequence; the inputs required, which include data such as the set of measured transmission values; the actual computing sequence and the outputs from that sequence, which may include data required for subsequent cycles of the computing sequence, as well as the desired output values for measurement and control purposes. The computing sequence is described using the common constructs of a high level language, such as For . . . Next and Repeat . . . Until loops, but it is not actually written in any particular language and uses verbal description rather than algebraic expressions. For ease of identification sections of the computing sequence are numbered using lower case Roman numerals in parentheses.

TABLE 1

CONSTANTS
$\lambda_i$ wavelengths for values of i from 1 to k.
$\eta_i$ refractive indices at each wavelength.
$v_i$ increment of trial value.
INPUTS
$t_{mi}$ measured transmittances at each wavelength.
rh upper limit of trial optical path value.
rl lower limit of trial optical path value.
COMPUTING SEQUENCE
(i) For trial value = vl to rh step vi
   For waveband No. (i) = 1 to k step 1
   Compute theoretical transmittance $t_{ci}$
   Next i
   Compute and Store Correlation coefficient.
   between set of $t_{ci}$ and $t_{mi}$
   Next trial value
(ii) Search for highest correlation coefficient.
   Actual Value = Trial Value which produced the highest correlation coefficient.
(iii) Calculate new upper and lower trial value limits.
OUTPUTS
   Actual Value (of optical path)
   vh
   vl

TABLE 2

CONSTANTS
$\lambda_i$ wavelengths for values of i from 1 to k.
$\eta_i$ refractive indices at each wavelength.
$v_i$ increment of trial value
er uncertainty in optical absorption gauge measurement of optical path.
INPUTS
$t_{mi}$ measured transmittances at each wavelength.
COMPUTING SEQUENCE
(i) Approximate optical path = a + b log $(t_{mp}/t_{mq})$
   where a & b are constants & $t_{mp}$ & $t_{mq}$ are 2 of the measured transmittances with significantly different absorptions.
(ii) Upper limit vh = approximate optical path +er.
   Lower limit vl = approximate optical path −er.
(iii) For Trial Value = vl to vh step vi
   For Waveband No. (i) = 1 to k step 1.
   Compute theoretical transmittance $t_{ci}$
   Next i
   Compute and Store Correlation coefficient between set of $t_{ci}$ and $t_{mi}$
   Next trial value
(iv) Search for highest correlation coefficient.
   Actual Value = Trial Value which produced the highest correlation coefficient.
OUTPUTS
   Actual Value (of optical path)

TABLE 3

CONSTANTS
$\lambda_i$ wavelengths for values of i from 1 to k.
$\eta_i$ refractive indices at each wavelength.
$v_i$ increment of trial value.
$v\eta$ nominal or approximate trial value.

TABLE 3-continued

INPUTS

$t_{mi}$ measured transmittance at each wavelength.

COMPUTING SEQUENCE

(i) Divide set of transmittances into 2 groups, $t_{mi}$ to $t_{mj}$ and $t_{m(i+1)}$ to $t_{ml}$ and calculate mean wavelength for each group $\lambda_{m1}$ and $\lambda_{m2}$ respectively (ii) For trial value = $v\eta$ to $v\eta + (\lambda_{mi}/2)$ step $vi$
For waveband No. i = 1 to j step 1
Compute theoretical transmittance $t_{ci}$
Next i
Compute & Store correlation coefficient between set of $t_{ci}$ and $t_{mi}$ (For i = 1 to j)
Next trial value (iii) Search for highest correlation coefficient and identify trial value that produces it, $t_{vi}$ (iv) Generate a set of values around $t_{vi}$ at a spacing of $(\lambda_{m1}/2)$ (v) ⎫ Identical sequence to (ii), (iii), (iv) save that
(vi) ⎬ calculation done using group 2, $t_{m(j+1)}$ to $t_{mk}$
(vii) ⎭ and $(\lambda_{m2}/2)$ (ix) Look for coincident or near coincident value or values between the 2 sets of values.

(x) Select the coincident value with the highest correlation coefficient in both groups as the actual value.

OUTPUTS

Actual Value.

Unless it is otherwise stated, in Tables 1–3 and in the associated text, the computing sequences that apply to transmission measurements also apply to reflection measurements. By replacing the expressions for measured and calculated transmittance, $t_{mi}$ and $t_{ei}$ with their equivalents for measured and calculated reflectance, $r_{mi}$ and $r_{ei}$ the necessary conversion is readily made.

The first example, shown in Table 1 describes the computing sequence for the measurement of a single optical path, (for example the optical thickness of a single film) in which the first set of signals representing the measured intensities is treated as a single group. (The use of an operating sequence of this type was earlier described as the 'brute force' method). In Table 1 we consider the measurements to have been made in a series of relatively narrow wavebands centered on wavelengths identified by the suffix i, which can take integer values from 1 to k, the number of wavelengths used.

In Table 1 the constants are the set of centre wavelengths, $\lambda_i$, the refractive index for the direction in which the light is propagated through the sample for each of these wavelengths, $n_i$ and the increment of trial value at which the trial calculation will be repeated $vi$. In Table 1 the inputs are the set of measured transmittance values $t_{mi}$ and the upper and lower limits of the range of trial value $v^h$ and $vl$ respectively.

Part (i) of the computing sequence uses two For . . . Next loops, one within the other. The outer loop variable is the trial value $vt$, which is incremented from $v^l$ to $v^h$ in steps of $vi$. The inner loop variable is the waveband suffix i which is incremented from 1 to k in steps of 1. Within the inner loop the calculated transmittance is computed and stored, using the current values of i and $vt$ and the appropriate values of wavelength and refractive index $n_i$. Once calculated transmittances for all wavebands have been computed within the inner loop, the correlation coefficient is calculated between the set of measured transmission values $t_{mi}$ and the set of calculated transmission values $t_{ei}$, according to the correlation equation (6) as previously defined. This correlation coefficient is stored for all values of the trial value In part (ii) of the computing sequence the set of stored correlation coefficients is searched to find the highest. The trial value which has produced this highest correlation is identified. It can be assumed that this trial value corresponds to the actual value, so the actual value is set equal to the said trial value.

In part (iii) of the computing sequence, if the measurement is being carried out on-line and if it may be assumed that the next value to be measured will not differ greatly from that just calculated, new upper and lower limits of the range of trial values $vh$ and $vl$ may be calculated from this actual value.

The description above with reference to Table 1 contains the implicit assumption that the transmittance (or reflectance) of the sample can be calculated from wavelength and refractive index measurements alone. This is a reasonable assumption if the sample does not absorb light in any of the wavebands. However, this is not a necessary requirement and by providing an absorption coefficient k as well as a refractive index $n_i$ at each of the wavelengths $\lambda_i$, the system of Table 1 may be made to operate correctly upon absorbing samples. (Alternatively the refractive index $n_i$ may be treated as a complex number: such a method, which will give equivalent results is well known in Optics).

The second example, shown in Table 2, describes the computing sequence for the measurement of a single optical path, in which the first set of signals representing measured intensities is treated as a single group and in which there is significant absorption caused by the sample in one or more of the measurement wavebands, and in which known optical absorption gauging means are used to determine the range of trial values.

In Table 2 the constants are the set of centre wavelengths $\lambda$, the refractive index $n_i$ and the absorption coefficient $k_i$, for the direction in which the light is propagated through the sample, for each of these wavelengths, the increment of trial value $vi$ at which the trial calculation will be repeated, and the maximum uncertainty in the optical path measurement for the optical absorption gauge measurement, er.

In Table 2 the inputs are the set of measured transmittance values $t_{mi}$.

Part (i) of the computing sequence comprises a calculation of the approximate optical path, according to known optical absorption gauging means, such as the equation shown which relates optical path to 2 constants a and b and the ratio of 2 of the measured transmission signals, which represent wavebands with significantly different absorptions caused by the sample.

In part (ii) of the computing sequence the upper and lower limits of the range of trial values are determined from the approximate optical path and the uncertainty in the optical absorption gauge measurement.

Parts (iii) and (iv) of the sequence in Table 2 correspond to parts (i) and (ii) of the sequence in Table 1.

The third example, shown in Table 3 describes the computing sequence for the measurement of a single optical path in which the first set of signals representing the measured intensities is divided into two groups, the spectral wavebands being chosen so that the mean wavelengths of the two groups differ. The operation of this sequence may be understood by referring to FIG. 6.

FIG. 6 shows plots of correlation coefficient against trial value for a sample of optical thickness 10 microns. Upper curve, (1) represents the correlation coefficient for a group of wave centered on 2.0 microns and lower curve (2) for a group centered on 1.6 microns.

It will be seen that in both cases the correlation coefficient oscillates in an approximately cosinusoidal way, especially around the target value. In the case of the group of wavebands centered around 2.0 microns, the correlation coefficient oscillates with a period of 1.0 microns and in the case of the wavebands centered around 1.6 microns the oscillation is at a period of 0.8 microns.

Whilst identifying the maximum correlation coefficient value in either upper or lower curve is difficult in that the peak values only decay slowly when the trial value changes to either side of the actual value, if we impose the condition that the trial value that gives a peak must be the same for both groups of wavebands, then the number of choices is greatly reduced. In the case of FIG. 6, possible values would be restricted to 6, 10 and 14 microns, and the correlation coefficient for 6 and 14 microns could be expected to be noticeably lower than for the correct value of 10. There is of course no necessity to use groups of wavebands whose centre wavelengths lead to a coincidence after a few peaks, although this may be convenient.

Noting that the correlation peaks around the trial value are regularly spaced leads to an important simplification in the form of calculation, in that for either group of wavebands, once one correlation peak has been located the trial values can be determined corresponding to those adjacent by multiple addition or subtraction of the spacing, which is one half of the mean wavelength. This can provide a massive reduction in the amount of computation required.

In Table 3 the constants are as for Table 1, save that we may add a nominal value, which conveniently may be the last computed actual value.

In Table 3 the inputs are the set of measured transmittances.

The computing sequence of Table 3 requires the wavelengths to be divided up into 2 groups. For each group a trial value that yields a correlation coefficient maximum is identified (as in FIG. 6) but over a very limited range of trial value, equal to one half of the mean wavelength of the group. It is known that provided the group is spread over a relatively limited spectral range (for example + or −10% of the mean wavelength), then other correlation maxima will appear to either side of the one identified, at a regular interval of half the said mean wavelength.

Thus two arrays of possible solutions are generated, one for each group. The groups are then searched for coincident or near coincident trial values. In general the coincident or near coincident trial value which exhibits for both groups the highest correlation is the one which corresponds to the actual value. Because the spacing of correlation maxima is not exactly half the mean wavelength of the group, increased accuracy may be obtained by treating the actual value derived in Table 3 as an approximate value, and reverting to the computing sequence of Table 1 for a very limited range of trial values around this approximate value.

It is evident that this technique of identifying coincidences between arrays of trial values derived from groups of measuring wavelengths is not limited to just two groups, but could be extended to three or more. In such a situation, where coincidences between all groups are obviously rarer, multiple solutions which needed resolution by considering the magnitude of the correlation would be relatively unimportant.

If the mathematical function that describes the transmittance or reflectance of the film can be written in a form that can be differentiated with respect to the optical path value, then correlation maxima can be identified by correlation zeros in the correlation between the measured intensities and the differential.

For example, from equation (11) differentiation with respect to optical thickness (ng) yields $$\frac{dT(\lambda)}{d(ng)} = -\frac{4\pi}{\lambda} \sin(4\pi ng/\lambda) \qquad (13)$$

Correlation of the measured transmittances with this function will yield a zero and a negative slope at the optical path which would have yielded a maximum in a correlation with $T(\lambda)$.

Referring to equation (6) it is apparent that the denominator will always be positive. Hence a zero in correlation coefficient must correspond to a zero in the covariance (equation 5)) and in the unnormalised covariance (equation 6)). Use of the latter is obviously simpler and saves computing time.

Equations (11) and (12) for transmittance and reflectance are simplifications, although if the measurement wavelengths are not too near to an optical absorption band or edge they may prove adequate. More sophisticated expressions and formulae are available in the optical literature, for example in "The Optical Properties of Thin Solid Films" by O. S. Heavens published by Butterworth Scientific Publications, in 1955, and the use of such expressions and formulae will improve accuracy.

Of the three examples described with reference to Tables 1, 2 and 3, only one incorporated absorption into the theoretical transmittance or reflectance calculation. In general the precision of the calculation will be improved if absorption is incorporated, although on thinner samples there may be no necessity to do so.

According to one embodiment of this invention the method of seeking a correlation maximum between measured and theoretical transmittance or reflectance values may be used to determine the composition of a sample. For this to be achieved effectively it will in general be necessary for the set of wavelengths used to include at least one located at or near an absorption band or edge for the material, and good results will be obtained if the set of wavelengths includes several on both long and short wavelength sides of an absorption band, which permits the characteristic dispersion of refractive index across the absorption band to provide an extra factor differentiating between the materials of which the sample may be made.

One method of determining the composition of a sample comprising a single material is as follows.

Firstly for all possible materials the optical constants (refractive index and absorption coefficient) must be stored within the computing means.

Secondly, using the data for one of the materials, or some average artificial material whose optical properties can be defined, but which may not exist, the optical path is determined by one of the methods described with reference to Tables 1, 2 or 3 or a similar method.

Thirdly, over a limited range of optical path around the value determined in the second stage above, the optical path should be calculated by the same or a similar method, for all the possible materials in turn and the correlation coefficient noted for each of the materials. The material whose optical constants yield the highest correlation coefficient is the one of which the sample is composed.

Using this method a single measurement may not be reliable and the measurement should be repeated until there is adequate statistical evidence as to which material is the correct one.

The description above has related primarily to transmission measurements, but the techniques described are equally applicable to measurements by reflection.

According to another embodiment of this invention, the measurements can be made of optical paths and optical thicknesses in compound or laminated materials and co-extruded materials. The methods described above may be used to measure the optical path within a layer within such a compound structure provided that there exist sufficient refractive index differences at the boundaries of said layer as to generate Fresnel reflections which will give rise to optical interference effects.

If the above-described embodiments of the invention are applied to a multilayer material, and the correlation computed for the transmitted intensities for a single layer, correlation maxima may be found for the optical paths corresponding to any pair of boundaries which generate Fresnel reflections. This number will be as great as $(q^2-q)/2$ where q is the number of layers in the material. Each of these optical paths represents the optical path in an individual layer or a sum of such paths. It is obvious that we will always have more equations as sums of optical paths than we have unknown optical paths, and in general computing means may be used to determine the structure of the material.

Where a given layer is bounded by one layer of lower refractive index (or air) on one side and a higher refractive index on the other side, interference effects in its transmission or reflection spectra will be of opposite polarity to the case when the layer is bounded by two materials of higher or lower refractive index. This phenomenon is very useful in distinguishing between layers in a multilayer material.

A further means whereby this invention can measure the optical paths within a multicomponent sample is to utilise the 'brute force' method described previously, not for all trial values in a given range, but for all combinations of trial values of all the components within given ranges. Certain constraints can be imposed, such as the fact that the highest trial value giving a satisfactory correlation on the basis of a single layer calculation must be equal to the total optical path.

In the case of determining a property, such as thickness, of a multilayered material, a model may be employed which enables the transmission or reflectance of the material to be computed from a knowledge of its structure and component materials whilst the more sophisticated expressions and formulae can be used as mentioned above (e.g. in the O. S. Heavens' reference), the method is complicated because, for 'q' layers, 'q' trial thickness values are required to cover the variation in thickness of the component layers.

Compared with optical absorption gauging means, the selection of wavelengths for the measurement in which optical interference effects are used is relatively uncritical. Further, compared with optical absorption gauging means there is greater freedom to choose the operating wavelength region, since there is no restriction to absorption regions.

In practice the wavelengths should be chosen so as to extend over about one cycle of the optical interference pattern for optical paths at the low end of the measuring range, which implies extension over a number of cycles at the high end and spacing should not be at regular intervals in wavenumber.

The criteria for the selection of measurement wavebands provide a means of enhancing the power and selectivity of this technique. Where measurements are made in a substantially absorption free region of the spectrum then the coherence length of the light beams used must be greater than the optical path within the sample in order to achieve adequate interference effects. It is evident that this permits the measurement to select a small optical path in the presence of a large one, such as a thin coating on a thick substrate, since the bandwidths can be chosen so that no interference will be observed between the faces of the thick substrate.

When one material is sorbed onto the surface of another it forms a layer whose thickness may be determined by an embodiment of this invention which uses reflection from the sample of material.

When one material is distributed inside another, it will affect the optical characteristics of the host material, either by changing the spectral absorption, spectral scattering or polarisation, or by changing the average refractive index. All or any of these optical changes may be measured by an embodiment of this invention. It is necessary that the change can be described in terms of a model relating the optical characteristics of the material to the property, or the identity of the sample which is to be sensed or determined. This model may be based on known theoretical characteristics of the sample or it may be empirically determined. One means of empirically determining a model is to present samples of known properties or identity to the instrument and to record the measured values so derived. Model values may be derived by interpolation from the recorded measured values.

In one embodiment of this invention the model values of transmittance or reflectance may be derived from measurements upon samples whose properties or identities are known, using a group of beams of light having the same optical properties as the group of beams which is used to measure the transmission or reflection of the sample whose properties or identity are or is unknown. Both groups of beams may conveniently be derived from the same source, or sources and may be separated by known optical beamsplitting means or may represent a division in time of a single group of beams, in which case a common detector system can be used. For example, if the optical thickness of an unknown sample is to be determined, model values of transmittance or reflectance may be derived from a set of samples of known optical thickness, or more conveniently, a single sample of wedged thickness, so that measurements appropriate to a range of thicknesses may be generated by moving it relative to the groups of beams. Such measurements may be made prior to the apparatus being used to measure the unknown sample, and the results stored, or they may be made continuously during the operation of the apparatus. For such an apparatus to determine the identity of a sample it would be necessary for it to make such measurements using a set of wedged samples of differing materials, each of which must be used to generate a set of trial values. The material of the unknown sample will be that of the known which yields the highest correlation at the appropriate optical thickness. In this instance it would be necessary for the apparatus to determine optical thickness before determining identity. This is not necessarily so for some other parameters, for example, anisotropy may be independent of thickness and single samples of each material would be sufficient if identity were determined by way of anisotropy. Such a method and apparatus has the advantage of reducing the amount of computation by providing measured rather than computed trial values of transittance or reflectance and also obviates the need for a model describing the optical properties of the sample material or materials to be determined. However, it does not eliminate the need for the wavelengths, polarisations or orientations of the beams to be chosen so as to give a sufficient change in correlation coefficient as the trial value is scanned through the actual value.

What is claimed is:

1. A method of sensing or determining a characteristic feature of a sample, the method comprising the steps of:
   (a) selectively utilizing electromagnetic radiation whose optical character is changed by said sample due to an optical effect which is at least one of optical interference, absorption, or scatter;
   (b) causing said electromagnetic radiation to be directed to said sample whereby the optical character of said radiation is changed as a result of the relevant transmission or reflection by said sample, the selection of said radiation being such as to include at least three discrete components selected from a spectral range so that at least one of said components is subjected to said optical effect so that said optical character is changed;
   (c) measuring the relevant transmittance or reflectance of said sample for each of said components to derive respective measured values;
   (d) correlating said measured values with different known values of relevant transmittance or reflectance, said different known values representing different values of known characteristic features of a known material or materials; and
   (e) selecting the known values having an optimum correlation with said measured values, the selected known values representing the characteristic feature of the sample which is sensed or to be determined.

2. A method according to claim 1 wherein said components are selected so that where said radiation is subjected to:
   (a) interference, said components have an irregular wavenumber or mean wavenumber spacing;
   (b) absorption, at least two of said components are located at or adjacent to an absorption band or edge for the sample so that at least three of said components are relatively and differently absorbed by said sample;
   (c) scatter, at least three of said components are scattered by different amounts by said sample.

3. A method according to claim 2 wherein the wavenumber spacing of said components is given by minimum redundancy linear sequences or Golomb rulers.

4. A method according to claim 1 wherein at least one mathematical model is used to derive said different known values.

5. A method according to claim 4 wherein said optimum correlation is a zero correlation value in the correlation between measured values and known values derived from a differential function of said model or models.

6. A method according to claim 4 when applied to a sample having an unknown magnitude to be sensed or determined, the method further including the steps of:
   using said measured values to provide a first estimation of the unknown magnitude;
   setting limits to a range of magnitudes containing said first estimation as a mean value;
   using the limited range of magnitudes in the mathematical model or models to compute said known values; and
   sequentially reducing the limits of said range depending on said correlation of known values and measured values.

7. A method according to claim 4, wherein said radiation is subject to optical interference and wherein:
   (a) correlation coefficients are computed between said measured values and the known values derived from the mathematical model or models for two or more groups of said radiation components, each said group including said selection of said at least three components;
   (b) the highest correlation coefficient is determined for each group of said radiation components over a limited range of known magnitudes used in said mathematical model or models to derive said known values;
   (c) the highest correlation coefficients derived from said latter step (b) are used to compute magnitudes at which peaks occur in the correlation coefficients for each of said groups; and
   (d) the known values are selected at the known magnitudes where the correlation coefficient peaks are coincident, or most nearly coincident.

8. A method according to claim 7 which is employed when there is more than one magnitude at which the correlation coefficients are coincident, or nearly coincident, the method further including the steps of limiting the range of known magnitudes to those providing said coincident or most nearly coincident peaks and selecting, from the limited range, the known values at the known magnitude at which the correlation coefficients are highest.

9. A method according to claim 1 wherein said radiation components are selected so that they have at least one of:
   (i) respectively different wavelengths, the bandwidth of each component being less than the difference between adjacent wavelengths, or
   (ii) respectively different angles of incidence, or
   (iii) respectively different polarisations, or
   (iv) combinations thereof.

10. A method according to claim 1 wherein the characteristic feature to be determined is the amount of anisotropy in the sample, said known values representing the transmittance or reflectance values of predetermined amounts of anisotropy over a predetermined range of anisotropies.

11. A method according to claim 1 which is initially employed to determine the optical thickness of the sample and which is subsequently employed to provide the identity of the sample, said known values taking account of said optical thickness before correlating said measured values with said known values to determine said identity.

12. A method according to claim 1 wherein the characteristic feature to be determined is the thickness of the sample.

13. A method according to claim 1 wherein the sample is a substance having a sorbed material, the quantity of the sorbed material being the characteristic feature to be determined.

14. A method according to claim 1 wherein the sample is a composition, the structure or at least one constituent of the composition being determined or sensed.

15. A method according to claim 1 which is initially employed to identify the sample and which is subsequently employed to determine the optical thickness of the sample, said known values taking account of said identity before correlating said measured values with said known values to determine said thickness.

16. A method according to claim 1 wherein said known values are derived by an analog technique in which said electromagnetic radiation is directed to a material similar to the sample and having different known magnitudes of a characteristic feature of the sample to be sensed or determined.

17. A method according to claim 1 wherein said known values are derived by an analog technique in which said electromagnetic radiation is directed to different known materials having different known magnitudes of the characteristic feature to be sensed or determined.

18. A method for sensing or determining a characteristic feature of a sample, the method comprising the steps of:
 (a) selectively utilizing electromagnetic radiation whose optical character is changed by said sample due to an optical effect which is at least one of optical interference, absorption, or scatter;
 (b) causing said electromagnetic radiation to be directed to said sample, said radiation including at least three components having respectively different properties;
 (c) measuring the relevant transmittance or reflectance of said sample for each of said radiation components to derive respective measured values;
 (d) providing known model values of relevant transmittance or reflectance as an output from at least one mathematical model into which is input (i) known values relating to the properties of the radiation components, and (ii) different magnitudes of the characteristic feature to be sensed or determined, said model taking account of the relevant absorption and interference and/or scatter;
 (e) correlating said measured values with said output model values; and
 (f) selecting the output model values having an optimum correlation with said measured values, the selected output model values representing the characteristic feature of the sample which is sensed or to be determined.

19. A method for sensing or determining a characteristic feature of a sample comprising the steps of:
 (a) selectively utilizing electromagnetic radiation whose optical character is changed by said sample due to an optical effect which is at least one of optical interference, absorption, or scatter;
 (b) causing electromagnetic radiation to be directed to said sample, said radiation including at least three components having respectively different properties;
 (c) measuring the relevant transmittance or reflectance of said sample for each of said radiation components to derive respective measured values;
 (d) computing model values on the basis of a differential function of a mathematical model to which are input (i) known values relating to properties of the radiation components, and (ii) different magnitudes of the characteristic feature to be sensed or determined and from which said model values are output;
 (e) correlating said measured values with said computed output model values;
 (f) determining optimum correlation from a zero correlation value in the correlation between said measured values and said computed output model values; and
 (g) selecting the computed output model values at which the correlation is optimum as the values which represent the characteristic feature of the sample which is sensed or to be determined.

20. A method for sensing or determining a characteristic feature of a sample comprising the steps of:
 (a) selectively utilizing electromagnetic radiation whose optical character is changed by said sample due to an optical effect which is at least one of optical interference, absorption, or scatter;
 (b) causing electromagnetic radiation to be directed to said sample, said radiation including two or more groups of radiation components, each group including at least three components having respectively different properties;
 (c) measuring the relevant transmittance or reflectance of said sample for each of said radiation components to derive respective measured values;
 (d) providing known model values of relevant transmittance or reflectance as an output from at least one mathematical model into which is input (i) known values relating to the properties of the radiation components, and (ii) different magnitudes of the characteristic feature to be sensed or determined;
 (e) computing correlation coefficients between said measured values and said output model values for said two or more groups of radiation components;
 (f) determining the highest correlation coefficient for each of said groups of radiation components over a limited range of known magnitudes;
 (g) deriving the highest correlation coefficients from the latter step (f) and using them to compute the magnitudes at which peaks occur in the correlation coefficients for each of said groups; and
 (h) selecting the output model values at the known magnitudes where the correlation coefficient peaks are coincident, or most nearly coincident.

21. A method according to claim 20 which is employed when there is more than one magnitude at which the correlation coefficients are coincident, or nearly coincident, the method further including the steps of limiting the range of known magnitudes to those providing said coincident or most nearly coincident peaks and selecting, from the limited range, the model values at the known magnitude at which the correlation coefficients are highest.

22. Apparatus for sensing or determining a characteristic feature of a sample utilizing electromagnetic radiation selected to be subject to an optical effect which is at least one of optical interference, absorption, or scatter, the apparatus comprising:
 (a) means for causing said electromagnetic radiation to be directed to said sample, said radiation including at least three discrete components selected from a spectral range so that at least one of said components is subjected to said optical effect so that the optical character of said component is changed;

(b) means for receiving the relevant transmitted or reflected radiation components and for providing corresponding measurement values;

(c) means for providing different known values of relevant transmittance or reflectance, said different known values representing different values of known characteristic features of a known material;

(d) means for determining the correlation between said measured values and said known values and for selecting the known values having an optimum correlation with said measured values, the selected known values representing the characteristic feature of the sample which is sensed or to be determined.

23. Apparatus according to claim 22 wherein means (b) is detector means for providing signals representing respective measurement values, the apparatus further including means for converting said measurement values into digital form; and wherein means (c) and (d) are computing means programmed with a mathematical model to which is input known magnitudes relating to the radiation components and different magnitudes of the characteristic feature of the sample to be sensed or determined in order to derive said known values, said computing means correlating said measured values with said known values and selecting the optimum correlation.

24. Apparatus according to claim 23, wherein the computing means is programmed to select the highest correlation coefficient as optimum.

25. Apparatus according to claim 23 wherein the computing means is programmed to identify a zero correlation value in the correlation between said measured values and said known values derived from a differential function of the model to which said magnitudes relating to the radiation components and said different magnitudes of the characteristic feature of the sample are input.

26. Apparatus according to claim 23, wherein said computing means automatically limits the range of known magnitudes on the basis of a first estimated value derived from said measurement values.

27. Apparatus according to claim 23, further including means for providing a respective measurement value or values from which a first estimation of the characteristic feature of the sample can be determined, the latter means being additional to said means for causing said radiation to be at least one of transmitted through or reflected from the sample, said computing means using said estimated value as a basis for automatically limiting the range of said magnitudes.

28. Apparatus according to claim 23, wherein said computing means is programmed:

(a) to compute correlation coefficients for two or more groups of said radiation components, each said group including said selection of said at least three or more components having relatively different properties;

(b) to determine the highest correlation coefficient for each group of said radiation components over a limited range of known magnitudes;

(c) to use the maximum correlation coefficients derived from the latter determination to compute the magnitudes at which peaks occur in the correlation coefficients for each of said groups; and (d) to select the model values at the known magnitude where the correlation coefficient peaks are coincident, or most nearly coincident.

29. Apparatus according to claim 28, wherein the computing means is further programmed to limit the range of known magnitudes to those providing said coincident or most nearly coincident peaks and to select, from the limited range, the model values at the known magnitude at which the correlation coefficients are highest.

30. Apparatus according to claim 22 including means for storing said known values, said means containing stored values which have been derived by relevant transmission or reflection of said electromagnetic radiation by a material similar to the sample having different known magnitudes of a characteristic feature of the sample to be sensed or determined.

31. Apparatus according to claim 22 including means for storing said known values, said means containing stored values which have been derived by relevant transmission or reflection by different known materials having different known magnitudes of the characteristic feature to be sensed or determined.

32. Apparatus for sensing or determining a characteristic feature of a sample utilizing electromagnetic radiation selected to be subject to an optical effect which is at least one of interference, absorption, or scatter, the apparatus comprising:

(a) means for causing said electromagnetic radiation to be directed to said sample, said radiation including at least three components having respectively different properties;

(b) means for receiving the relevant transmitted or reflected radiation components in order to provide measured values of the relevant transmittance or reflectance, and for converting said measured values into digital form;

(c) computing means programmed with at least one mathematical model to which is input known values relating to the properties of the radiation components and different magnitudes of the characteristic feature to be sensed or determined in order to output model values, said model taking account of said optical effect, said computing means correlating said measured values with said model values and selecting the model values with the optimum correlation as representative of the characteristic feature of the sample to be sensed or determined.

33. Apparatus for sensing or determining a characteristic feature of a sample utilizing electromagnetic radiation selected to be subject to an optical effect which is at least one of interference or absorption, the apparatus comprising:

(a) means for causing said electromagnetic radiation to be directed to said sample, said radiation including at least three components having respectively different properties;

(b) means for receiving the relevant transmitted or reflected radiation components in order to provide measurement values and for converting said measurement values into digital form;

(c) computing means programmed with at least one differential function of at least one mathematical model to which is input known values relating to properties of the radiation components and different magnitudes of the characteristic feature to be sensed or determined in order to output model values, said computing means being further programmed to determine optimum correlation from a zero correlation value in the correlation between said measured values and said output model values.

34. Apparatus for sensing or determining a characteristic feature of a sample utilizing electromagnetic radiation selected to be subject to an optical effect which is at least one of interference, absorption, or scatter, the apparatus comprising:
  (a) means for causing said electromagnetic radiation to be directed to said sample, said radiation including at least three components having respectively different properties;
  (b) means for receiving the relevant transmitted or reflected radiation components in order to provide measurement values and for converting said measurement values into digital form;
  (c) computing means programmed (i) with at least one mathematical model to which is input known values relating to the properties of the radiation components and different magnitudes of the characteristic feature to be sensed or determined in order to output model values, (ii) to compute correlation coefficients between said measured values and said output model values for two or more groups of said radiation components, (iii) to determine the highest correlation coefficient for each group of said radiation components over a limited range of known magnitudes, (iv) to derive the highest correlation coefficients from the latter step and to use them to compute the magnitudes at which peaks occur in the correlation coefficients for each of said groups, and (v) to select the output model values at the known magnitudes where the correlation coefficient peaks are coincident, or most nearly coincident.

35. Apparatus according to claim 34 wherein said computing means is further programmed to limit the range of known magnitudes to those providing said coincident or most nearly coincident peaks and selecting, from the limited range, the model values at the known magnitude at which the correlation coefficients are highest.

* * * * *